(12) United States Patent
Coppens et al.

(10) Patent No.: US 9,179,880 B2
(45) Date of Patent: Nov. 10, 2015

(54) RADIATION THERAPY PATIENT COUCH TOP COMPATIBLE WITH DIAGNOSTIC IMAGING

(75) Inventors: Daniel D. Coppens, Avondale, PA (US);
David M. Rabeno, Bear, DE (US);
Malcolm W. Kroeber, Hockessin, DE (US)

(73) Assignee: QFIX SYSTEMS, LLC, Avondale, PA (US)

( * ) Notice: Subject to any disclaimer, the term of this patent is extended or adjusted under 35 U.S.C. 154(b) by 0 days.

(21) Appl. No.: 11/535,055

(22) Filed: Sep. 25, 2006

(65) Prior Publication Data

US 2007/0074347 A1   Apr. 5, 2007

Related U.S. Application Data

(60) Provisional application No. 60/719,777, filed on Sep. 24, 2005, provisional application No. 60/795,836, filed on Apr. 27, 2006, provisional application No. 60/809,256, filed on May 30, 2006, provisional application No. 60/815,920, filed on Jun. 23, 2006, provisional application No. 60/835,854, filed on Aug. 4, 2006.

(51) Int. Cl.
*A61B 6/00* (2006.01)
*A61B 6/04* (2006.01)
*A61N 5/10* (2006.01)

(52) U.S. Cl.
CPC ....... *A61B 6/0442* (2013.01); *A61N 2005/1061* (2013.01)

(58) Field of Classification Search
CPC .......................................... A61B 6/00

USPC ...................... 5/600–601; 378/209
See application file for complete search history.

(56) References Cited

U.S. PATENT DOCUMENTS

| 3,980,288 | A | * | 9/1976 | Mitchell et al. ................... 5/601 |
| 4,261,436 | A |   | 4/1981 | Stillman, Jr. |
| 4,557,127 | A |   | 12/1985 | Pietrelli |

(Continued)

OTHER PUBLICATIONS

International Search Report for PCT/US06/37250, dated Mar. 25, 2008.

*Primary Examiner* — Frederick Conley
(74) *Attorney, Agent, or Firm* — RatnerPrestia

(57) ABSTRACT

A radiation therapy patient couch top which provides optimal fields of treatment in a high-energy radiation therapy environment. In addition, the patient couch top provides superior imaging qualities when used in a diagnostic imaging x-ray environment. All metal is eliminated from the treatment/imaging area. This ensures that no metal will be in the way of the radiation treatment beam and that no artifacting will occur when used with diagnostic imaging techniques such as Computed Tomography. By employing moveable fiber reinforced support beams, the main patient support structure can be positioned so that a minimum of electron generation will occur through Compton scattering. By allowing for a removable insert, the top patient surface can be optimized for treatment, diagnostic imaging or the addition of other useful features. The novel design of these inserts allows the tip end of the beams to be free from any cross members, further improving the imaging and treatment qualities of the resulting patient couch top. Further, a CT simulator insert is provided which provides the same dosimetric properties for the patient couchtop and devices during patient treatment planning.

27 Claims, 14 Drawing Sheets

(56) References Cited

U.S. PATENT DOCUMENTS

| | | | |
|---|---|---|---|
| 4,575,064 A | 3/1986 | Menor | |
| 5,537,454 A | 7/1996 | Korver | |
| 5,778,047 A * | 7/1998 | Mansfield et al. | 378/209 |
| 5,806,116 A | 9/1998 | Oliver et al. | |
| 6,161,237 A | 12/2000 | Tang et al. | |
| 6,378,149 B1 * | 4/2002 | Sanders et al. | 5/624 |
| 6,526,609 B2 | 3/2003 | Wong | |
| 6,598,275 B1 | 7/2003 | Kolody et al. | |
| 6,669,143 B1 | 12/2003 | Johnson | |
| 6,832,400 B2 * | 12/2004 | Loveday et al. | 5/601 |
| 6,904,630 B2 | 6/2005 | AlKassim | |
| 6,955,464 B1 * | 10/2005 | Tybinkowski et al. | 378/209 |
| 7,020,917 B1 * | 4/2006 | Kolody et al. | 5/621 |
| 7,063,461 B2 | 6/2006 | Coppens et al. | |
| 7,076,821 B2 | 7/2006 | De Mooy | |
| 7,120,223 B2 * | 10/2006 | Nafstadius | 378/20 |
| 2004/0034932 A1 | 2/2004 | Zacharopoulos et al. | |
| 2004/0133979 A1 * | 7/2004 | Newkirk et al. | 5/600 |
| 2004/0133980 A1 | 7/2004 | Coppens et al. | |
| 2006/0185087 A1 | 8/2006 | Coppens et al. | |

* cited by examiner

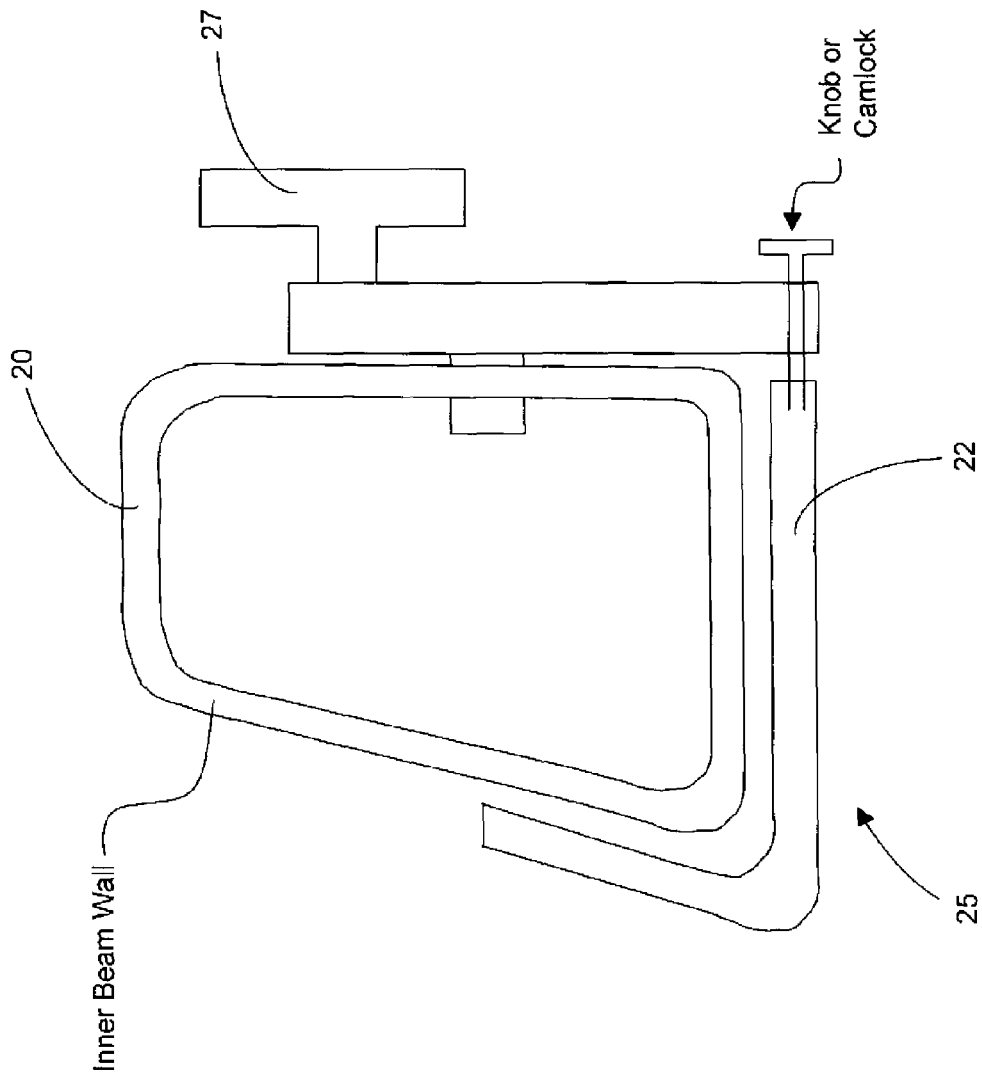

Typical beam cross-sections that reduce or eliminate artifacting in CT applications

- Any beam can be turned upside down
- Convex or concave on either side
- Stealth Beam Technology ™

RADIATION THERAPY PATIENT COUCH TOP COMPATIBLE WITH DIAGNOSTIC IMAGING

This application claims the benefit of U.S. Provisional Application 60/719,777 filed 24 Sep. 2005; U.S. Provisional Application 60/795,836 filed 27 Apr. 2006; U.S. Provisional Application 60/809,256 filed 30 May 2006; U.S. Provisional Application 60/815,920 filed 23 Jun. 2006; and U.S. Provisional Application filed Aug. 4, 2006 60/835,854.

BACKGROUND OF THE INVENTION

State of the art cancer radiation therapy is increasingly based on the pinpoint application of high-energy radiation, which is highly tailored to the shape and position of the cancerous tumor. Modern techniques such as IMRT use a pencil sized treatment beam whose cross-section is shaped to match the tumor. This allows the physician to spare the surrounding healthy tissue while increasing the treatment dose to the cancerous target. As the size of the treatment beam decreases, the accurate location of the beam becomes much more critical. If a highly tailored beam is off target by a few millimeters, it may miss the tumor entirely.

Because of these new techniques, it becomes increasingly desirable to know the position and shape of the tumor accurately with the patient in the exact position that he will be at the time of treatment. For this reason, manufacturers of radiation therapy machines are increasingly combining their machines with built in diagnostic imaging capability. Advances such as On Board Imaging (OBI) and Cone Beam CT allow the development of treatment plans using tumor diagnostic imaging data while the patient is in the exact position and constraining configuration as during treatment. Image Guided Radiation Therapy (IGRT) techniques in which diagnostic imaging as well as treatment beams are used require that the couch top perform well in both modes.

Traditionally, patient treatment plans have been performed on a separate simulation machine, which uses diagnostic imaging either through static images or CT imaging. The patient is placed on a radiolucent tabletop also referred to as a couch top in the language of the industry. The patient couch top for diagnostic imaging application are optimized to provide minimum X-ray absorption in the 50 to 150 kVp range and are generally of a monocoque foam core/carbon fiber skin construction. Radiation Therapy patient tables generally operate in the 6 MeV to 25 MeV x-ray energy range (for photon energy treatment). At this energy level, an effect known as Compton Scattering occurs. As the photons pass through the couch top material, electrons are given off which then impact the patient. Electrons do not penetrate deeply into the human body but are rather absorbed by the skin and can cause skin reactions. For this reason, great care is taken in the design of Radiation Therapy patient couch tops to minimize the Compton Scattering effect. Consequently, couch tops developed for Radiation Therapy are generally of a different configuration than those made for diagnostic imaging.

SUMMARY OF THE INVENTION

The present invention overcomes the deficiencies of previous couch tops and provides a radiation therapy patient couch top consisting of a frame containing at least two moveable radiolucent support beams that extend into the treatment/imaging area and move laterally on one linear bearing way (the lower portion of the couch top). By providing a structure, which does not require a connection between the support beams at the tip end of the couch top, no metal or other features exist that can reduce the image quality and interfere with a high-energy radiation treatment beam. The invention further provides for an upper couch top portion, which creates the patient support surface. The upper couch top portion consists of an aft panel, a locking cartridge and an integrated, removable radiolucent inserts, which sits on top of the exposed portion of the support beams for supporting the patient in the treatment/imaging area. The aft section, locking cartridge and insert are connect to each other so that their locations to each other are dimensionally accurate and repeatable when the insert is attached and removed.

The present patient couch top performs well both in diagnostic imaging and radiation therapy environments (including photon, proton and electron radiation therapy). In a preferred embodiment, the patient couch top is completely free of metal in the treatment/imaging area. The treatment/imaging area is that portion of the couch top that can be accessed by the treatment of imaging radiation beam.

Specifically, in one embodiment, the present invention provides a radiation therapy patient couch top with one or more removable components comprising a frame comprising two or more moveable radiolucent beams that extend into a treatment/imaging area and move laterally, wherein the beams are free from a connecting element that span and connect the beams in the treatment/imaging area; and a patient supporting radiolucent insert that can be secured accurately and repeatably to the frame.

In another embodiment, the present invention provides a radiation therapy patient couch top comprising a frame comprising one radiolucent beam that extends into a treatment/imaging area that moves laterally on only one linear bearing way.

In yet another embodiment, the present invention provides a radiation therapy patient couch top comprising a frame comprising only one radiolucent beam that extends into a treatment/imaging area that moves laterally on two or more linear bearing ways.

In yet another embodiment, the present invention provides a method of imaging a tumor, planning treatment and treating the tumor comprising the steps of:
 a. placing a patient in a simulator containing an upper couch top portion;
 b. acquiring an image;
 c. planning the radiation treatment by optionally digitally removing portions of a CT insert that do not represent the treatment couch, and optionally digitally adding back any features that might be present in the treatment couch top; and
 d. treating the patient on a patient treatment machine.

BRIEF DESCRIPTION OF THE DRAWINGS

FIG. 6 illustrates a cross-section of a clamp secured to a support beam.

DETAILED DESCRIPTION OF THE INVENTION

Figure 1A:
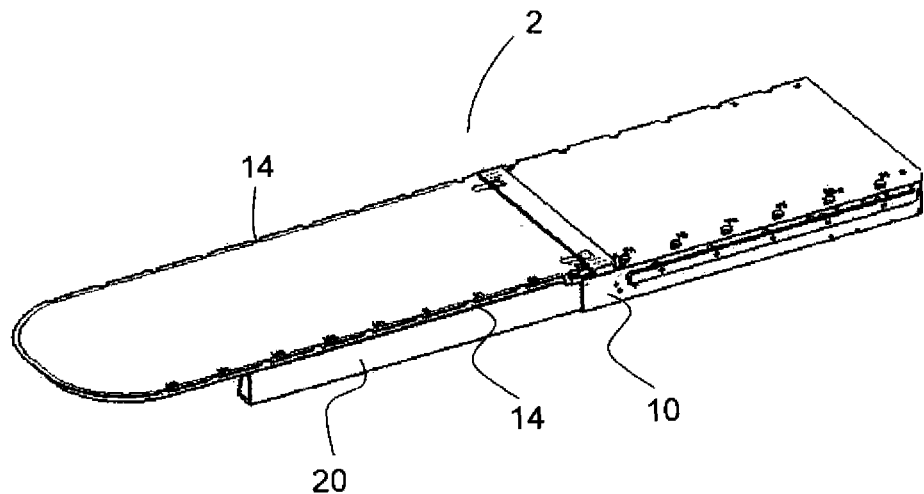
FIGS. 1A-1D illustrate a couch top of the present invention.
Figure 1B:
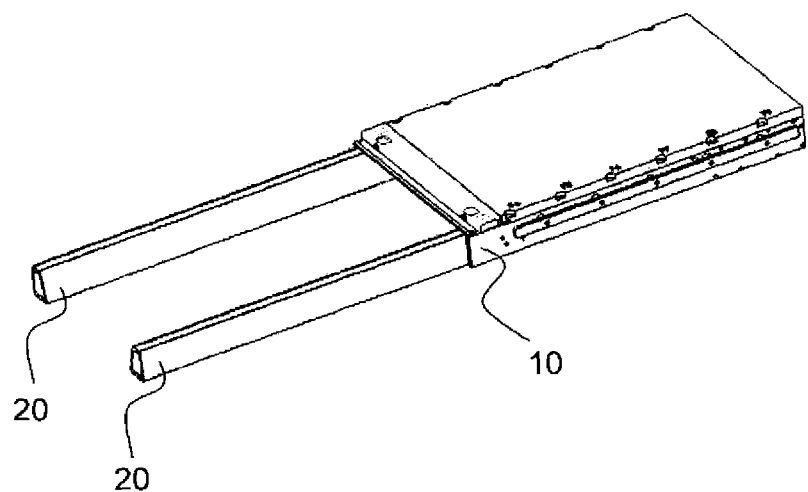
Figure 1C:
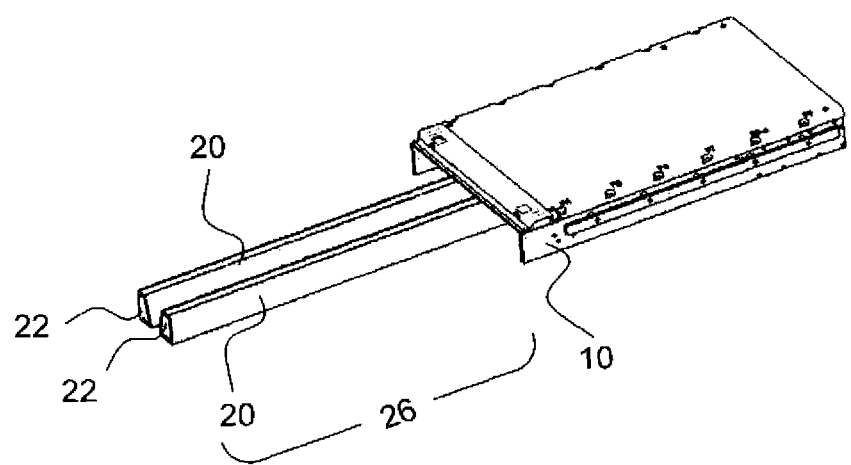
Figure 1D:
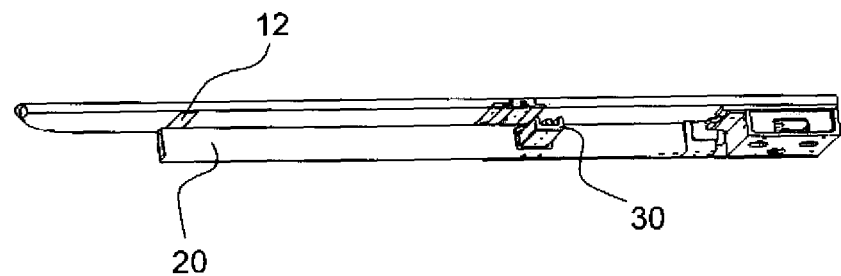

Current patient couch tops that use support beam construction (whether moving or fixed) rely on a connecting element, which spans and connects the beam tips. The insert panel loads are partially transferred to the beam tips and taken out through the beams by loading the beams in torsion. This becomes particularly important when either one or both support beams are placed in the inner position. We have discovered an alternate way to react these loads through the structure so that the beams can remain unconnected in the treatment/imaging area. With proper design, the insert panel can be constructed so that it has adequate structural integrity to carry the torsions loads itself.

The insert panel can be constructed so that it has adequate torsional structure by designing it to constitute a torsion box. The torsion box design provides structural integrity so that the support beams can be placed at their inner most positions, which leaves the insert surface unsupported at the corners. The torsion box approach allows structural integrity adequate for supporting patients in a variety of configurations include those of foreseeable misuse. One way to create the torsion box is to use an adequate number of composite material bias plies. For example, several plies may be placed on a substantially +/−45 degree orientation. +/−45 degree composite material orientation provides the most efficient material usage to create a torsion box for the insert panel. Ultimately, torsional properties are designed in for each specific insert application.

This tip configuration provides new opportunities for imaging and treatment and is superior to all existing patient couches designed for combined treatment and imaging. For example, head and neck treatments are no longer limited to the area of the head & neck that can be cantilevered beyond the tip end connection. Rather, treatments that start in the head region can be continued in one setup all the way down the spine, providing superior cranial-spinal access. Treatment of diseases such as medullo blastoma can be performed on a supine patient, speeding the process because the patient doesn't need to be rotated on to their stomach. Radiation beam field matching that is required can also be eliminated, increasing accuracy and causing less chance of over dosing the patient in the field matching region. Since the need to simulate treatment for the patient in more than one position is also eliminated, the patient receives less kV x-ray dosage as well. And, importantly, all of this is more comfortable for the patient as well.

One beneficial aspect of this invention is the compatibility of the couch top with configurations that can be place in a Computed Tomography (CT) machine for patient simulation and treatment planning. By pinning the aft cover panel to the locking cartridge, which is then accurately connected to the removable panels, all of the indexing features (if present) can be accurately aligned with minimal tolerance stacking. Since our invention includes an upper couch top portion of essentially uniform thickness, this portion can be used as a CT simulation insert with the same properties as the radiation therapy treatment couch top of this invention. Current CT simulation inserts simply create a 3D coordinate system, which does not mimic the patient treatment couch top or absorb x-rays in the same manner. Because this invention allows the same components to be placed in the CT, the patient support and immobilization structures are available during patient treatment planning from CT imaging data. These structures are the same as those that occur on the patient treatment machine. This is particularly beneficial when used in conjunction with the latest treatment methods such as IGRT (Image Guided Radiation Therapy). This aspect of the invention does not require that the treatment couch top support beams be moveable. In fact, the same CT simulation benefits would occur with a fixed beam construction with a similar upper couch top surface that can be placed onto a CT scanner. If desired, it is possible to take the support beams into account in the treatment planning software. However, with the moving beam solution, it is possible to simply move the beams out of the radiation treatment path so that it is not necessary to take them in to account.

Referring to FIGS. 1A-1D, the present invention consists of a radiation therapy patient couch top, comprising a frame 10, which provides a mounting means 50, for bolts to allow the patient couch top to be mounted to any couch base. At least two moveable structural fiber reinforced radiolucent support beams 20 extend from the frame 10 into the treatment/imaging field 26. The beams 20 are attached to the frame 10 through the use of a single linear bearing way 30, which runs transverse to the beams. This allows the beams to be moved from side to side so that they do not encumber the radiation treatment field 26. While the present diagrams do not illustrate motorized beams, the use of motor driven movement means for adjusting the support beams can be incorporated as one skilled in the art would readily recognize.

Figure 2:
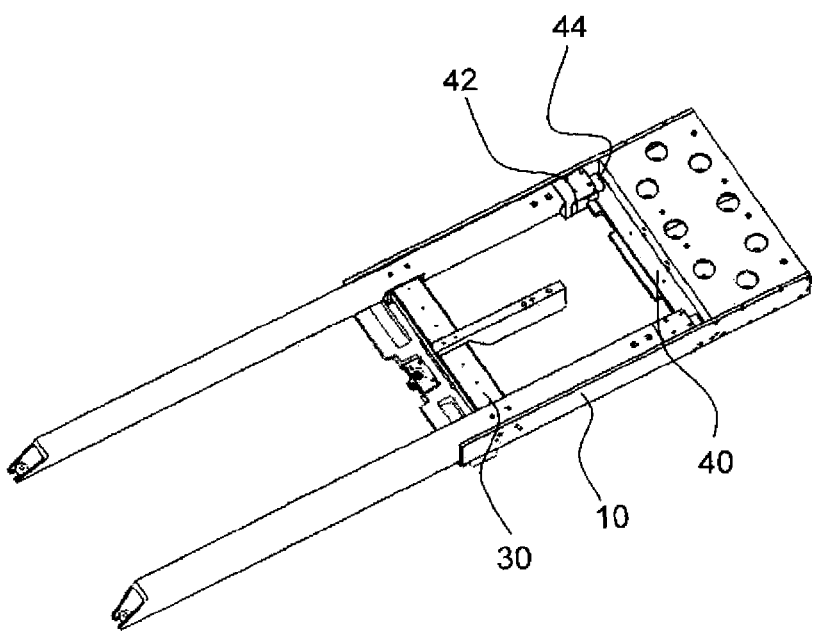
FIG. 2 illustrate the underside of the present invention.

Referring to FIG. 2, in a preferred embodiment, the linear bearing way 30 resides at the middle of the beams 20. At the rear end of the frame 10, beam loads are reacted against a flat load reaction surface 40. An adjustable block 42 is attached to the rear of each beam 20, which can be adjusted vertically. This allows any vertical play to be removed from the system, providing a rigid interface as the beams 20 are loaded with the weight of the patient. In addition, this adjustment allows the option for the beam front tips 22 to be slightly elevated so that when the patient is placed on the couch 2, any couch system deflection causes the beams to become horizontal. By attaching a cam follower 44 to each block 42, the smoothness of motion can be enhanced as the beams are positioned from side to side. By employing only one linear bearing way, an improvement is made over previous designs in that construction of the moving beam system does not require alignment of two or more linear bearing ways and the adjustability of the height can be accommodated. In addition, component cost is reduced.

Figure 5A:
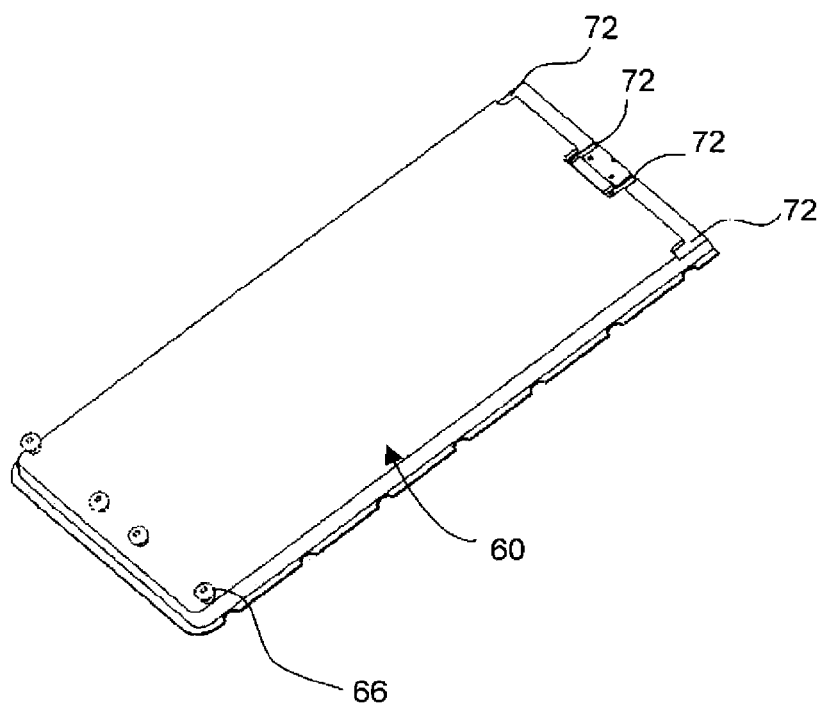
FIGS. 5A-5B illustrate an insert with locking pins.
Figure 5B:
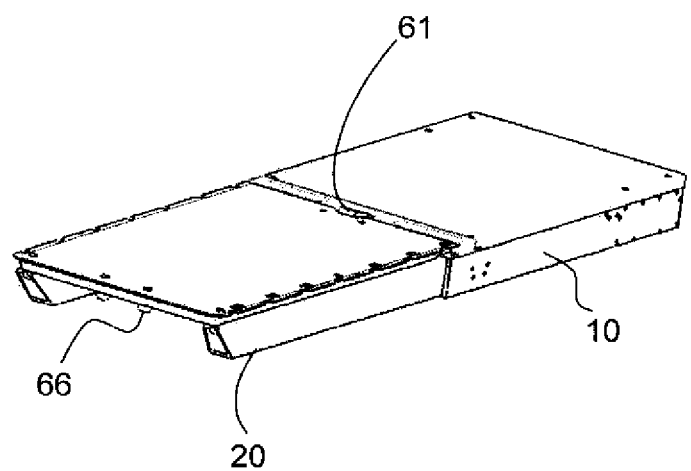

As shown in FIGS. 3A-3D, radiolucent inserts 60 are placed on top of the carbon fiber support beams 20 where the beams extend into the treatment/imaging field 26. These removable inserts create the upper portion of the couch top patient surface over the extended beams. The insert can be connected to the frame using a locking cartridge 61 which comprises any one of several locking means, including ½ turn lock, pin connection, latch, cam or clamp. The insert in this embodiment is attached to the frame with the engagement of a ½ turn locking mechanism 62. In this embodiment, the insert can be attached to the front of each beam as well. This is achieved by engaging locking pins 66, which are attached to the insert 60, into beam slots 68, which are machined into the front of each beam 20. The pins 66 provide a discrete location were the beams may be positioned with that particular device. This provides the advantage that the beams cannot move during treatment and they can be positioned accurately and repeatably in the same indexed location during patient treatment cycles that require multiple visits (treatment fractions). Each removable insert can have one or more discrete locations for each beam so that, for example as shown in FIG. 5, an inner and outer beam position may be provided for use with the particular insert. This allows for the beams to be placed preferentially in an outside position for treatments such as head and neck or pelvis, treatments that generally require clear beam access down the center of the patient. One or more of the beams can preferentially be placed at an inside position for treatment of tumors of the lung or breast.

In addition, FIGS. 3A-3D, 4, 5A, 5B and 6 show the locking pins 66, which attach the insert to the front of the beams with safety pins 70 that protrude up from the top of each beam 20. These safety pins 70 are positioned in such a way that a corresponding indentation or slot 72 is required to provide clearance on the bottom of the insert so that it may be installed on the couch top. This is provided as a safety feature so the insert can only be positioned and locked in place with the front end locking pins 66 engaged in the beam slots 68. The same result can be achieved by attaching material to the bottom of the insert panel, which blocks the lateral motion of the beams.

In another embodiment, the support beams 20 are free to move underneath the insert. This can be accomplished by providing a low friction surface 12 under the bottom of the insert FIG. 1D. The top of the beams 20 can then receive a corresponding low friction surface or pad, allowing the beams to be easily repositioned by hand with the patient in place on the couch top. This can also be accomplished by placing rollers in the top of the beams but this solution is less desirable because the resulting complication increases complexity and cost while reducing image quality. In fact the entire bottom surface can include a low friction surface.

One benefit that arises because the Couchtop is metal free in the treatment/imaging area is that the couch can be made compatible with MRI and radio frequency techniques. Carbon fiber is not compatible with these technologies because it is electrically conductive. However, other non-conductive fibers such as aramid, Ultra High Molecular Weight Polyethylene (UHMW), Spectra, fiberglass and others can be used by themselves or in combination (including with carbon fiber), to find a solution with structural integrity, which is compatible with RF, MRI and x-ray environments. One preferred embodiment that works well for both RF localization and x-ray treatment/imaging is to construct the support beam from aramid fiber in the top and sidewalls while constructing the bottom flange from carbon fiber. The carbon fiber is kept an adequate distance from the patient and is used on the compression side of the beam where aramid performs poorly. The aramid is placed close to the patient where RF interference is not acceptable. The inserts are then produced from aramid as well.

We have found that a variety of constructions can be used in the sidewalls of the beams to improve imaging and treatment performance as well as minimize CT artifacting. By using aramid materials (or another low density composite) in the sidewalls, the attenuation and artifacting can be reduced while maintaining a large degree of shear stiffness. Another excellent construction is to use plywood in the sidewalls as a core material. The plywood is extremely low density when compared to carbon fiber and even aramid, reducing the attenuation. In addition the plywood can be cut on a bias (45 degrees) so that the shear stiffness of the beam is maximized. Aramid honeycomb and foam may also be used but shear stiffness is reduced. Finally, at least one of the sidewalls of the support beams can be perforated to produce open area thereby reducing electron generation when exposed to high energy x-rays.

Figure 3A:
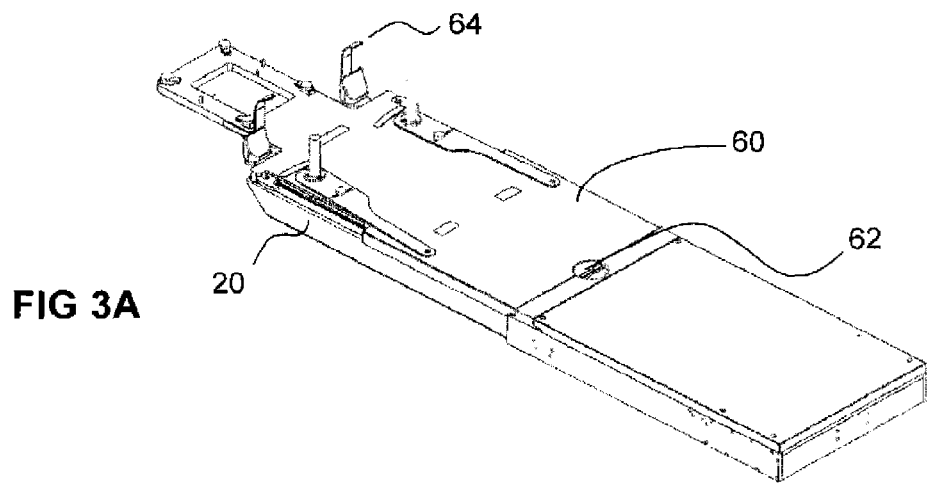
FIGS. 3A-3D illustrate various inserts for use with the present invention.
Figure 3B:
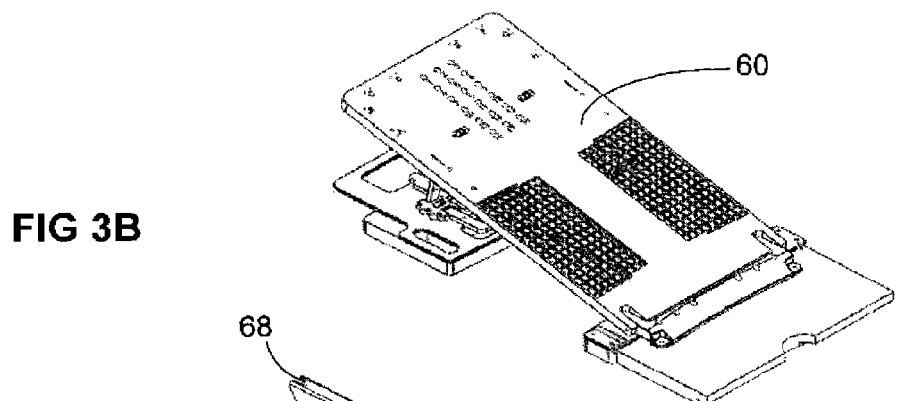
Figure 3C:
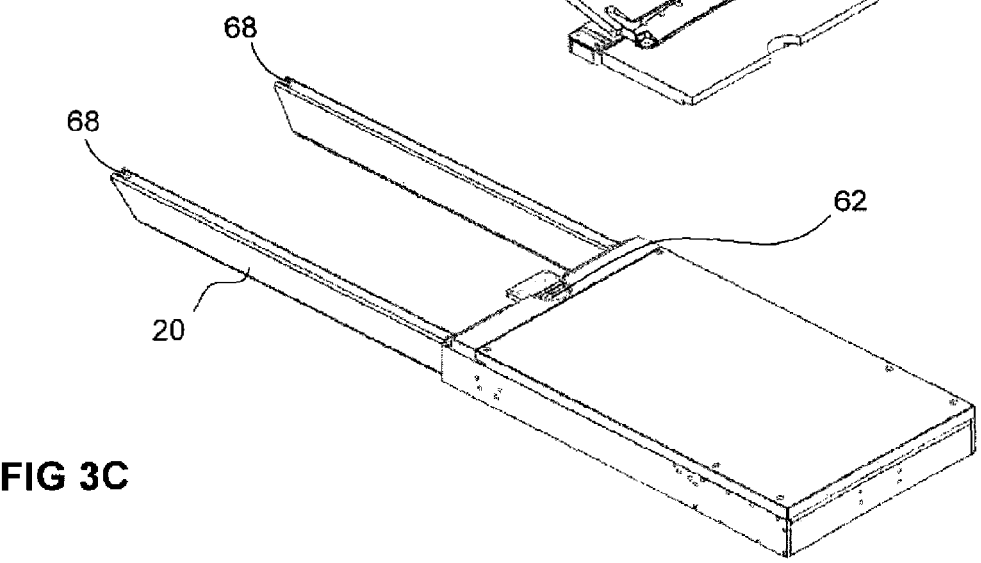
Figure 3D:
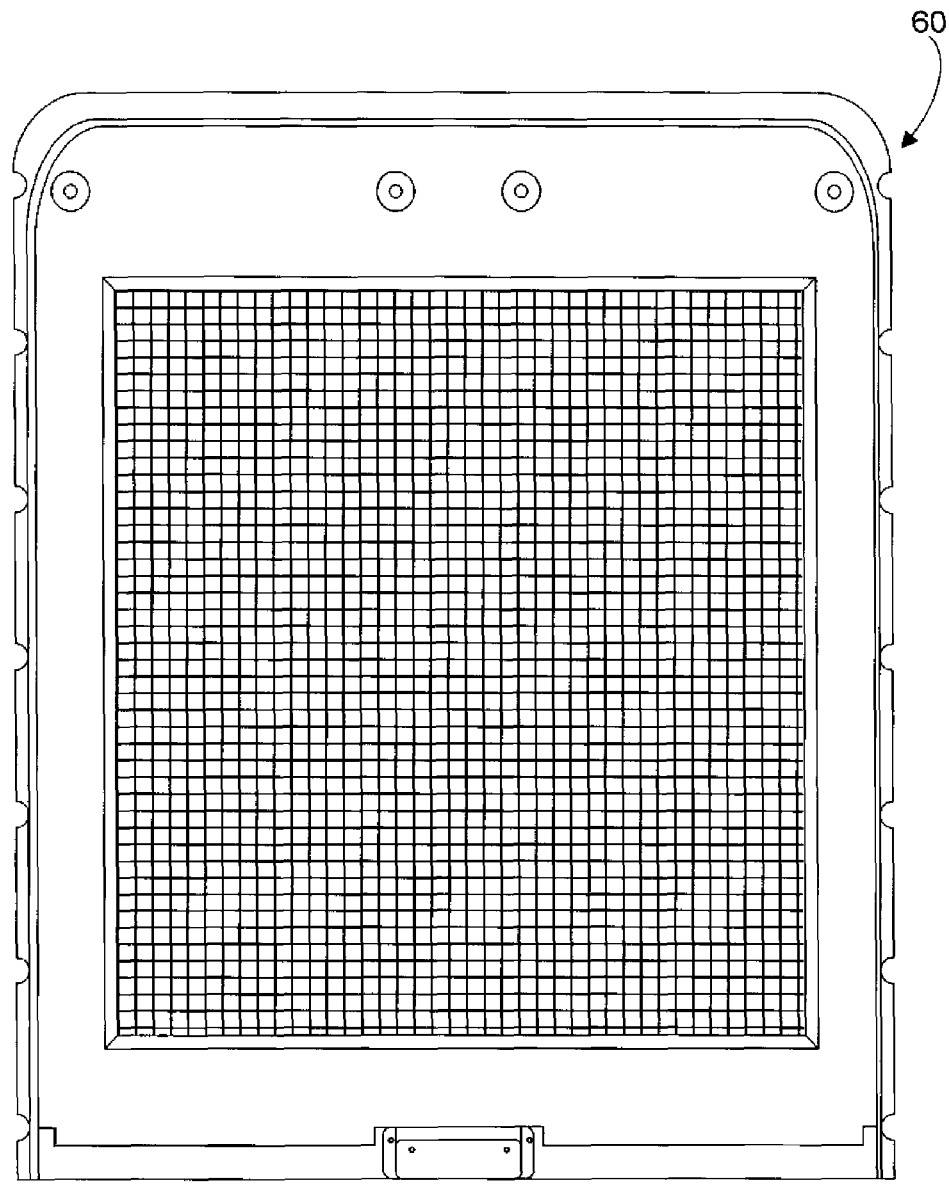
Figure 4:
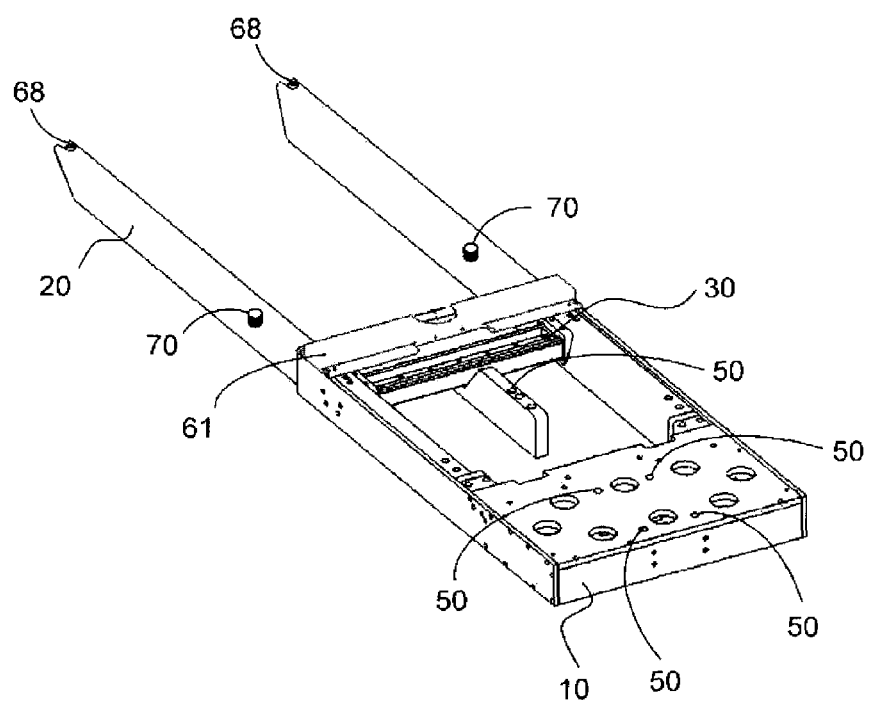
FIG. 4 illustrates the present invention without the aft panel or insert.

In a preferred embodiment, a trapezoidal support beam cross-section as shown in FIG. 6, having a narrower top than bottom creates a highly efficient structure because most composites are stiffer and stronger in tension than in compression. When placed under a patient load, the bottom of the beam is placed in compression. By optimizing the top and bottom flange, the neutral axis of the beam can be set to the middle of the beam, optimizing the stiffness, while minimizing the amount of material needed. This has both structural and x-ray attenuation benefits. In addition, by making one wall vertical, the machining of the beams, during construction, is simplified. The outward slope of the inner beam wall also means that any artifacting caused during Cone Beam CT is directed away from the patient. Additionally, less material is presented to the radiation beam at oblique angles. This provides a significant advantage when compared to the upside-down trapezoid and parallelogram geometries currently used. In a preferred embodiment of the invention, the support beams shown in FIG. 6 are manufactured from carbon fiber and have a cross-section as illustrated. Finally, by angling the inner wall of the beam toward the outside of the couch top, greater access is created to the bottom of the insert. This provides better patient visualization from underneath the couch top when a grid insert feature is used as shown in FIG. 3D.

Figure 7A:
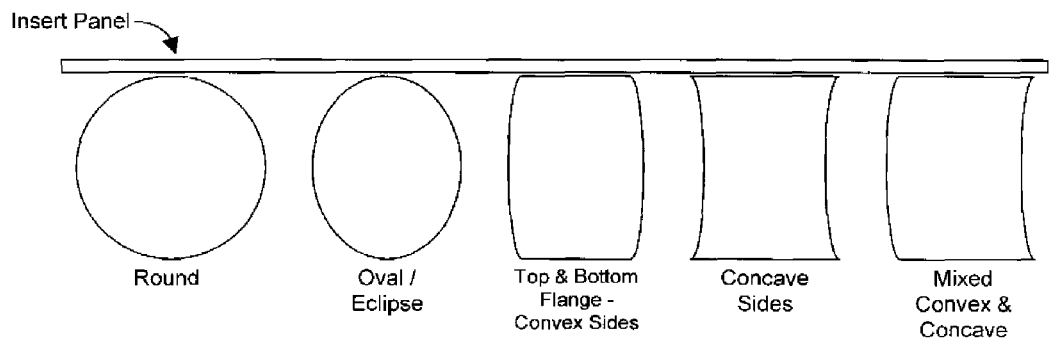
FIGS. 7A-7C illustrate several beam cross-sections.
Figure 7B:
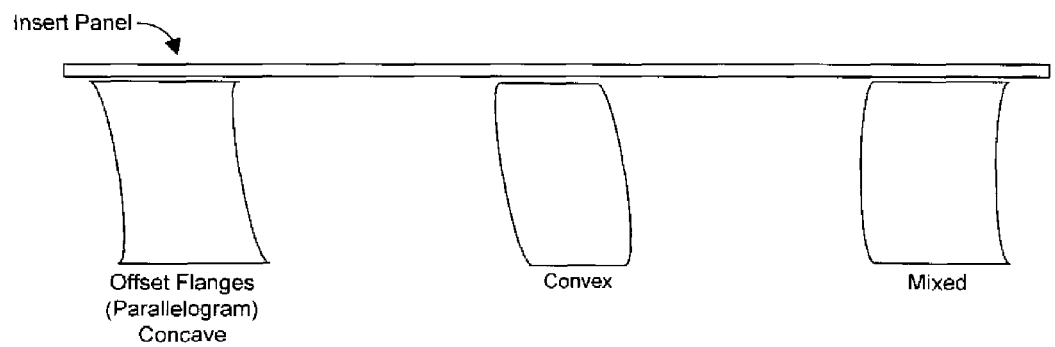
Figure 7C:
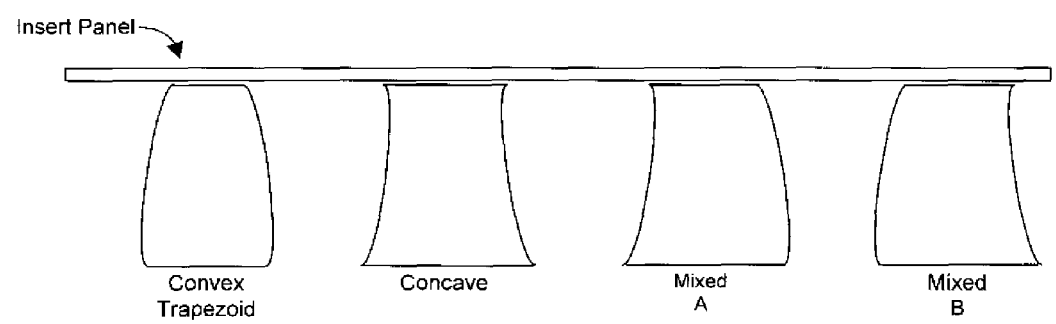
Figure 8:
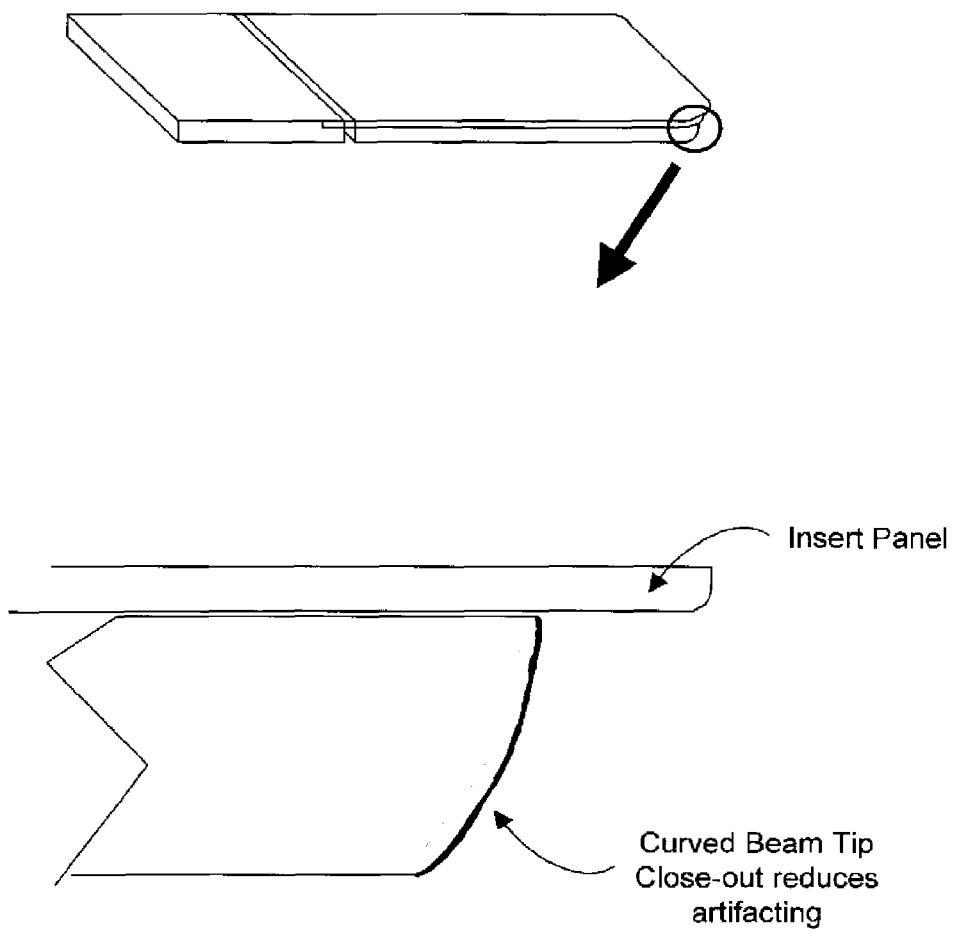
FIG. 8 illustrate the curved beam tip.

In addition, artifacting can be greatly reduced or eliminated by slightly curving the walls of the beam (when viewed in cross section) so that no straight walls exist to create artifacts. This is particularly useful in creating a "stealthy" support beam for use with Cone Beam CT. It is particularly beneficial to curve the substantially vertical sidewalls. Artifacting tends to project in a straight line from the straight wall. The substantially vertical walls, therefore, project their artifacts into the patient above the beam. Curving the horizontal flanges or portions of the beam is less beneficial since these portions of the beam generally do not artifact into the patient image. However, in circumstances of special inserts it can be beneficial for the flanges to be curved. Examples include prone breast inserts that allow the breast to fall below the plane of the flanges and patient conformal inserts that also fall below the plane of the flanges. FIGS. 7A-7C shows a variety of potential support beam cross sections, which reduce artifacting. Both concave and convex curvature is beneficial and the ultimate beam cross-section can be selected to optimize on such attributes as artifacting, structural integrity, and manufacturability. These geometry solutions can also be combined with the material solutions discussed above. Adding curvature to the tip of the beam, as illustrated in FIG. 8, whether the beam tip remains open or closed, can also reduce tip artifacting.

Inserts 60 are provided that can be tailored to the users needs. In its simplest form, the insert consists of a foam core/carbon fiber skin construction that performs well in a diagnostic imaging environment and is free of shadows and CT artifacting. Since the insert is thin (on the order of 1" thick), it is suitable for basic radiation therapy use as well. FIG. 3D illustrates another insert option consists of a carbon fiber frame with a thin carbon fiber center section that has been perforated to produce an open grid pattern, producing lower Compton scattering. This configuration reduces the stiffness of the surface and also creates diagnostic imaging disadvantages when static x-rays are used. Alternately, low electron generating surfaces can be produced, which have less stiffness reduction.

Low electron generation inserts can be produced for this Couchtop using the technology developed by Coppens, et' al. which is fully described in co-pending U.S. patent application Ser. No. 11/350,983 filed Feb. 8, 2006, hereby incorporated by reference. By orienting the face sheet material at +/−45 degrees, an insert can be produced that has torsional rigidity. To lower the electron generation to an absolute minimum, the insert can be design so that the support beams must be placed in the outer position. In this way face sheet fibers are needed primarily to span from one beam to the other and a minimum of material is required.

To any of these inserts 60, can be added provisions for patient immobilization. This is desirable so that patients can be positioned accurately and repeatably on the couch top. FIG. 3A shows another insert 60 containing features on which a low temperature thermoplastic mask can be directly attached. This figure also demonstrates that shoulder retraction features 64 can be embedded in the insert for enhanced patient immobilization. Additional embodiments as shown in FIG. 3B include an insert that incorporates pelvis immobilization, an insert which allows a patient's back to be placed at an angle to the couch for use in breast cancer treatment, an insert which allows radiation therapy of the breast with the patient in the prone position, and an insert that can be customized to provide superior access to the perineum for use in urological and Brachytherapy procedures.

To any of these inserts, indexing provisions 14 as shown in FIG. 1A can be added such as described in co-pending U.S. patent application Ser. No. 10/633,231 filed Aug. 2, 2003, to Coppens et al., hereby incorporated by reference, so that standard radiation therapy devices from any manufacturer can be used in conjunction with this invention.

An additional element of the invention is the inclusion of a removable clamp 25 as shown in FIG. 6. In a preferred embodiment the clamp accommodates a section of universal clamp rail 27. This allows the user to attach the clamp on the couch top when and only when it is needed while the beams 20 positioned in the outer position. In addition, it can be strategically placed so that it does not interfere with the imaging or treatment beam. Accessories such as IV poles, arm boards, stirrups or Brachytherapy delivery devices can thus be used with the couch top. FIG. 6 shows the clamp 25 attached to the support beam 20. However, a clamp 25 can also be used that attaches to the insert. The clamp can be configured so that its position with respect to the couch top can be infinitely variable. The clamp can also be configured so that it locks into indexed discrete positions. By allowing the clamp to be indexed to the couch top, it can be used to provide a releasable repeatable feature to locate devices required for treatment. A single clamp can include the features required to allow it to be both infinitely variable and indexable.

A tip extension can also be used so the length of the couch top can be increased as required. This is designed and constructed in such a way that no metal is added to the couch top. We have also included a provision to allow a phantom to be attached to the couch top for dosimetric and QA purposes.

Figure 9A:
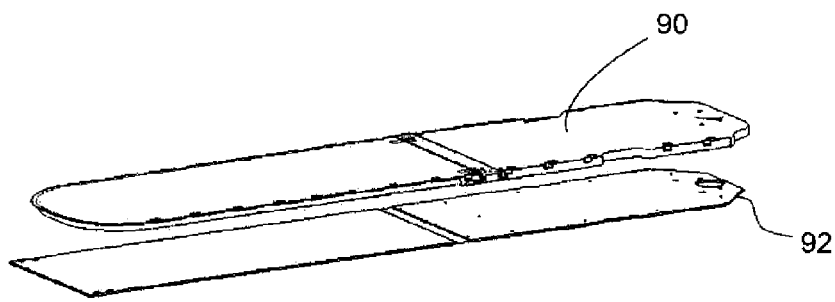
FIG. 9A-9C illustrate the CT assembly.
Figure 9B:
Figure 9C:
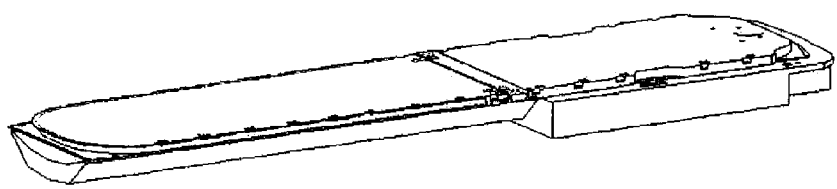
Figure 10:
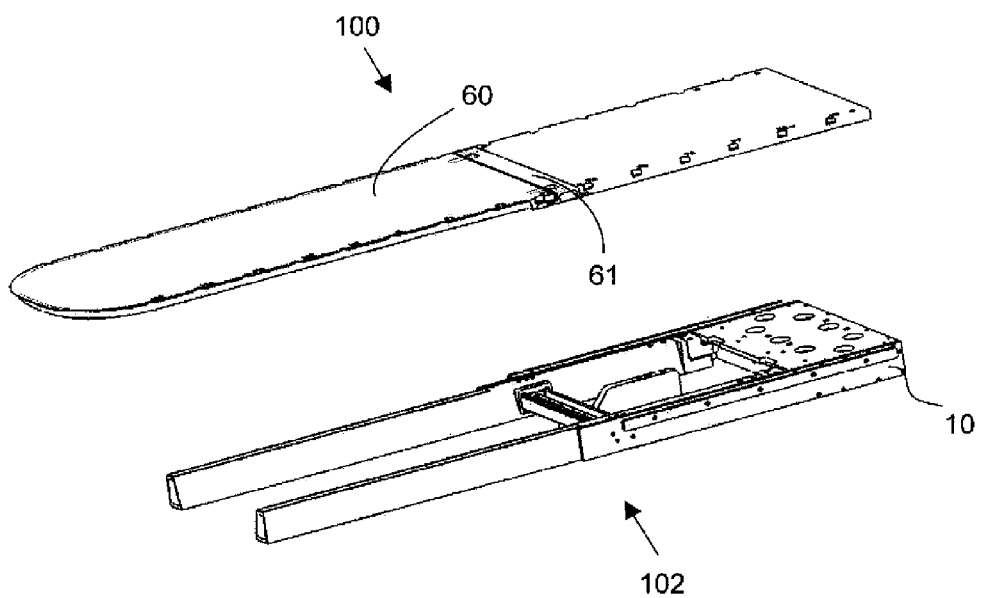
FIG. 10 illustrate the upper and lower portion CT insert with the platter.

Because we have designed the couch top to be separable in to an upper portion 100 and lower portion 102, as illustrated in FIG. 10, it becomes relatively easy to incorporate the design in to a CT simulator insert that employs the same patient positioning inserts and devices that will be used in treatment. In a preferred embodiment, as shown in FIGS. 9A-9C, the upper portion 90 of the couch top is mounted to a platter 92. This platter then interfaces to the CT cradle 94. By fabricating this platter from a material with adequately different x-ray attenuation (as measured in Hounsfield units on the CT image) than the couch top inserts, the platter can be "windowed" out of the CT image for patient treatment planning. This allows the patient planning software to identify the kVue treatment portions of the couch top only and account for them properly in the patient dose plan. This means that higher accuracy can be achieved in calculating the actual treatment energy dose, which reaches the tumor.

Although the support beams are not represented in the CT data, the support beams have fixed x-ray attenuation profile. Only their lateral location can change. This means that we can create a profile in the patient planning software (a template), which can then be placed in the proper lateral location so that it is taken in to account during treatment planning. If desired, an x-ray fiducial can be added to the platter so that the intended location of the beams is indicated in the CT data. The software template for the support beams can then be placed at that location. The fiducials can be made of thin wire or sheet material with the requirement that their attenuation is adequately different from the surrounding structures.

Figure 11:
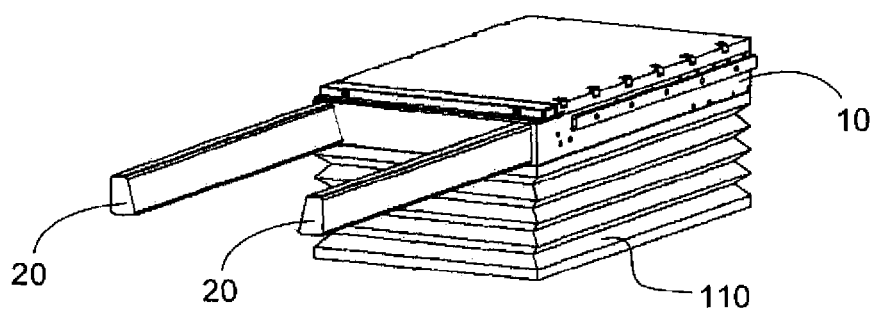
FIG. 11 the couch pedestal.

Since the couch top of this invention can be separated into a lower and upper portion, it is also possible to create a couch top that reduces the total combined height of the couch top and couch pedestal 110 as illustrated in FIG. 11. By mounting the support beams in front of the pedestal 110 it becomes possible to mount the upper portion of the couch to the top of the couch pedestal. This is a particularly useful embodiment when combined with the multi-degree of motion platforms that are becoming popular for radiation therapy. Since these platforms are generally mounted on top of the OEM couch pedestal, they constitute a pedestal extension. By incorporation the design described above, the combined thickness of the pedestal platform and couch top can be reduced. If the total thickness becomes too high, it may become impossible to bring the tumor down into the isocenter of the treatment machine and in range of the treatment beam.

This description and the Figures shown illustrate a few examples of the present invention and are in no way meant to be limiting. Several different specific designs are contemplated by the inventors without parting from the original scope of the present invention and would be easily recognizable by those skilled in the art. Whereas the invention has been shown and described in connection with the preferred embodiments thereof it will be understood that many modifications, substitutions and additions can be made which are within the intended broad scope of the following claims.

We claim:

1. A radiation therapy patient couch top with one or more removable components comprising:
 a frame comprising two or more moveable radiolucent beams that extend into a treatment/imaging area and move laterally on only one linear bearing way, wherein the only one linear bearing way runs transverse to the radiolucent beams, and wherein the beams are free from a connecting element that span and connect the beams in the treatment/imaging area; and
 a patient supporting radiolucent insert that can be secured accurately and repeatably to the frame;
 wherein the insert attaches to the frame and rests on the beams, wherein the beams can freely move laterally beneath the insert with and without the insert supporting a patient, and wherein a bottom surface of the insert comprises a low friction surface in contact with top surfaces of the beams such that the radiolucent beams are movable without moving the patient supported by the radiation therapy patient couch top.

2. The radiation therapy patient couch top of claim 1 further comprising an accessory clamp releasably attached to the insert.

3. The radiation therapy couch top of claim 1 wherein the beams have at least one wall and wherein at least one of the walls is perforated to produce open area, thereby reducing electron generation when exposed to high energy x-rays.

4. The radiation therapy patient couch top of claim 1 wherein the insert attaches to the frame, and wherein the couch top further comprises securing means for the beams so that the beams are prevented from moving thereby providing a discrete location for each beam.

5. The radiation therapy patient couch top of claim 1 wherein the beams have at least one wall and at least one of the walls comprise at least one selected from the group consisting of aramid, wood, low density material, honeycomb and foam.

6. The radiation therapy patient couch top of claim 1 further comprising a locking mechanism for connecting the insert to the frame, wherein the locking mechanism is at least one selected from the group consisting of a Vz turn lock, a pin connection, a latch, a cam and a clamp.

7. The radiation therapy patient couch top of claim 1 wherein one or more features are incorporated into at least one of the insert or beams so that the insert can only be attached to the couch top when the beams are in discrete locations.

8. The radiation therapy patient couch top of claim 1, wherein the radiolucent insert is at least one selected from the group consisting of a foam cored composite panel, an open grid, a low electron generation device, a releasable accessory device, a universal tip mount, and an integrated device for treatment of breast, head, neck or pelvic regions.

9. The radiation therapy patient couch top of claim 1 wherein the radiolucent insert further comprises securing means for accurately and repeatably attaching a radiation therapy device.

10. The radiation therapy patient couch top of claim 1 further comprising an accessory clamp releasably attached to one or more of the beams.

11. The radiation therapy patient couch top of claim 10 wherein the accessory clamp can be accurately and repeatably located on the support beam.

12. The radiation therapy patient couch top of claim 10 further comprising a section of universal clamp rail for attaching one or more accessories to the clamp and to the couch using the clamp.

13. The radiation therapy patient couch top of claim 1 wherein the beams comprise at least one composite material selected from the group consisting of carbon fiber, aramid fiber, PBT fiber, UHMW fiber, and fiberglass.

14. A radiation therapy patient couch top comprising:
a frame having two or more moveable radiolucent beams that extend into a treatment/imaging area that move laterally on only one linear bearing way;
the only one linear bearing way being arranged to run transverse to the radiolucent beams;
the moveable radiolucent beams being configured to move freely on the one linear bearing way and to move freely and laterally with respect to a patient support surface; and
wherein the radiolucent beams are substantially free of attachments to the patient support surface, permitting the radiolucent beams to move freely and laterally beneath the patient support surface and permitting the beams to be positioned at different locations in the treatment/imaging area,
and wherein a bottom surface of the patient support surface comprises a low friction surface in contact with top surfaces of the beams such that the radiolucent beams are movable without moving a patient supported by the radiation therapy patient couch top.

15. The couch top of claim 14, wherein the low friction surface comprises rollers.

16. The radiation therapy couch top of claim 14 wherein the beams have at least one wall and wherein at least one of the walls is perforated to produce open area, thereby reducing electron generation when exposed to high energy x-rays.

17. The couch top of claim 14, wherein a top surface of each of the radiolucent beams comprises a low friction surface.

18. The radiation therapy patient couch top of claim 14 further comprising at least one removable radiolucent insert that sits on top of an exposed portion of the beams for supporting a patient in the treatment/imaging area.

19. The radiation therapy patient couch top of claim 14 wherein the radiolucent insert contains adequate material oriented to create a torsion box thus allowing at least one beam to be placed at its innermost position while supporting the load of a patient on a corner of the couch top.

20. The radiation therapy patient couch top of claim 14 wherein the beams comprise at least one composite material selected from the group consisting of carbon fiber, aramid fiber, PBT fiber, UHMW fiber, and fiberglass.

21. A radiation therapy patient couch top of claim 14 comprising:
a frame comprising two or more moveable radiolucent beams that extend into a treatment/imaging area, wherein at least one beam has a top flange and a bottom flange and wherein a cross section of the top flange is narrower than a cross section of the bottom flange.

22. A radiation therapy patient couch top of claim 14 comprising:
a frame comprising two or more moveable radiolucent beams that extend into a treatment/imaging area, wherein at least one of the beams has a wall and a tip and wherein at least one of the wall and tip has a curvature to reduce CT artifacting.

23. The radiation therapy couch top of claim 22 wherein the curvature has a radius less than 50 cm.

24. The radiation therapy patient couch top of claim 14 wherein the beams have at least one wall and at least one of the walls comprise at least one selected from the group consisting of aramid, wood, low density material, honeycomb and foam.

25. A radiation therapy patient couch top comprising:
a frame containing at least two radiolucent support beams that extend into the treatment/imaging area, the beams being free from any element connecting or spanning the beams in the treatment/imaging area;
wherein each beam includes an artifact reducing surface, the artifact reducing surface being selected from the group consisting of a convex curve, a concave curve, and a non-vertical side wall; and
wherein a top surface of each beam comprises a low friction surface that contacts a bottom surface of the couch top such that the beams are moveable without moving a patient supported by the radiation therapy couch top.

26. The couch top of claim 25, wherein each beam includes an outer wall that extends vertically from the bottom side to the top side and each beam includes an inner wall that slopes toward the outer wall and extends from the bottom side to the top side.

27. A radiation therapy patient couch top comprising:
a frame comprising only one radiolucent beam that extends into a treatment/imaging area and being configured to move laterally on only one linear bearing way,
the only one linear bearing way being arranged to run transverse to the radiolucent beam; and the only one beam being configured to move freely beneath the patient couch top and without moving the patient couch top, wherein the only one beam is substantially free of attachments to a patient support surface, permitting the only one beam to move freely and laterally beneath the patient support surface and permitting the only one beam to be positioned at different locations in the treatment/imaging area;

wherein a top surface of the only one radiolucent beam comprises a low friction surface that contacts a bottom surface of the couch top such that the only one beam is movable without moving a patient supported by the radiation therapy patient couch top.

\* \* \* \* \*